Figure 1:
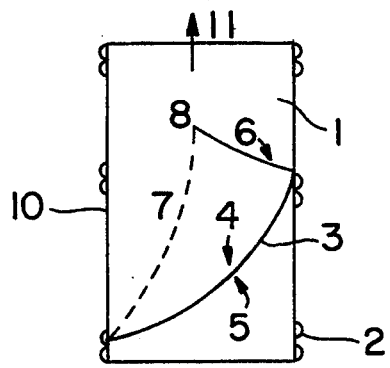
Figure 1A:
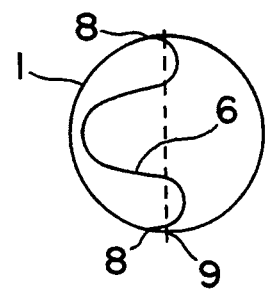
Figure 1B:
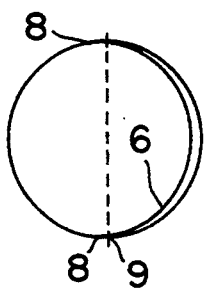

United States Patent [19]

Camilli

[11] Patent Number: 5,358,518
[45] Date of Patent: Oct. 25, 1994

[54] ARTIFICIAL VENOUS VALVE

[76] Inventor: Sante Camilli, Via Casole D'Elsa, 15, Rome, Italy

[21] Appl. No.: 8,823

[22] Filed: Jan. 25, 1993

Related U.S. Application Data

[63] Continuation of Ser. No. 802,611, Dec. 5, 1991, abandoned.

[30] Foreign Application Priority Data

Jun. 25, 1991 [IT] Italy .............. 000458 A/91

[51] Int. Cl.⁵ .............. A61F 2/24; A61F 2/54; F16K 15/00; F16K 17/00
[52] U.S. Cl. .............. 623/2; 623/66; 137/521; 137/527
[58] Field of Search .............. 623/2; 137/521, 527

[56] References Cited

U.S. PATENT DOCUMENTS

| | | | |
|---|---|---|---|
| 2,292,003 | 8/1942 | Yant et al. | 623/2 |
| 3,312,237 | 4/1967 | Mon et al. | 623/2 |
| 3,673,612 | 7/1972 | Merrill et al. | 623/2 |
| 3,717,883 | 2/1973 | Mosher | 623/2 |
| 3,744,062 | 7/1973 | Parsonnet | 623/2 |
| 3,877,080 | 4/1975 | Olcott | 623/2 |
| 3,903,548 | 9/1975 | Nakib | 623/2 |
| 3,969,130 | 7/1976 | Bokros | 623/2 X |
| 4,178,638 | 12/1979 | Meyer | 623/2 |
| 4,218,782 | 8/1980 | Rygg | 623/2 |
| 4,373,216 | 2/1983 | Klawitter | 623/2 |
| 4,406,022 | 9/1983 | Roy | 623/2 |
| 4,535,483 | 8/1985 | Klawitter et al. | 623/2 |
| 4,643,732 | 2/1987 | Pietsch et al. | 623/2 |
| 4,759,758 | 7/1988 | Gabbay | 623/2 |
| 4,829,990 | 5/1989 | Thuroff et al. | 128/79 |
| 4,851,001 | 7/1989 | Taheri | 623/2 |
| 5,032,128 | 7/1991 | Alonso | 623/2 |
| 5,080,668 | 1/1992 | Bolz et al. | 623/2 |

FOREIGN PATENT DOCUMENTS

| | | | |
|---|---|---|---|
| 2342102 | 2/1975 | Fed. Rep. of Germany | 623/2 |
| 1360724 | 12/1987 | U.S.S.R. | 623/2 |

*Primary Examiner*—Randall L. Green
*Assistant Examiner*—Dinh X. Nguyen
*Attorney, Agent, or Firm*—Young & Thompson

[57] ABSTRACT

An artificial venous valve with unidirectional flow, for insertion into the human venous system, biocompatible with the receiver, comprises a hollow elongated support and a plate carried by and within the hollow elongated support and movable relative to the support between a position to permit flow of blood in one direction and a position in which to prevent flow of blood in an opposite direction through the support. The plate is movable to open and close over a pressure differential range on opposite sides of the plate of 1–50 mm Hg.

3 Claims, 1 Drawing Sheet

ARTIFICIAL VENOUS VALVE

This application is a continuation, of application Ser. No. 07/802,611, filed Dec. 5, 1991, now abandoned.

The present invention refers to an artificial venous value, that is to say a device which, when inserted into a vein in the human body, permits a unidirectional, centripetal flow of blood; said device having the following main characteristics:
1. biocompatibility with the receiver;
2. mobility at low pressure;
3. antithrombogenic characteristics;
4. durability in time;
5. availability in various sizes, in various forms, in various materials;
6. availability for use in a sterile packaging.

An object of the present invention is the provision of a fixed prosthesis, with the function of a unidirectional valve to be inserted in the human venous system, of use in particular pathological conditions.

To date no device with the characteristics described above either is on the market or has been designed and proposed.

In human pathology, the "syndrome of chronic venous insufficiency" is known, essentially caused by venous hypertension and chronic venous stasis due to valvular incompetence both of a primitive nature (or primary or essential or idiopathic) and of a secondary nature following past illnesses of the venous system (generally speaking, deep venous thrombosis).

In the cases of venous valvular incompetence, the doctor has no efficacious drugs at his disposal, and the surgeon is not provided with artificial valves (whereas valves of various types for heart diseases, for cerebral decompression, for intestinal derivation, etc., have been available for many years).

Several methods of valvular plastic surgery, direct or indirect, at the present time allow the recovery of valvular function in certain cases; however the spread of said methods is obstructed by the delicate nature of the valvular structures or by the irreversible damage of the same.

At the present time no artificial venous valve can be found on the market or has been described in the literature.

The device whose provision is the object of the present invention is an artificial venous valve which allows the above problems to be solved.

The valve is made up of a cylindrical, or cylindroidal support, within which is inserted a mobile plate which moves with the variation of the pressure gradient on the two sides of the same, and which allows a unidirectional, centripetal flow of the venous blood.

The valve can be of a semirigid or rigid type.

Figure 2:
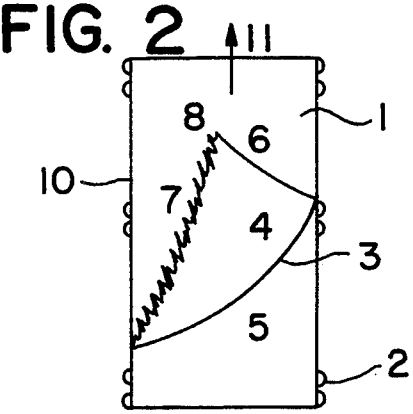
Figure 2A:
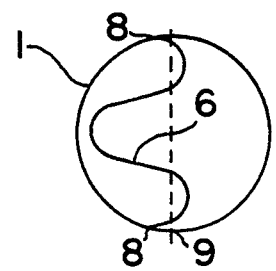
Figure 2B:
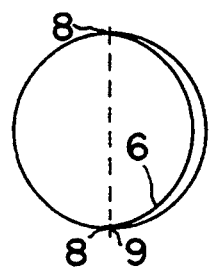
Figure 3:
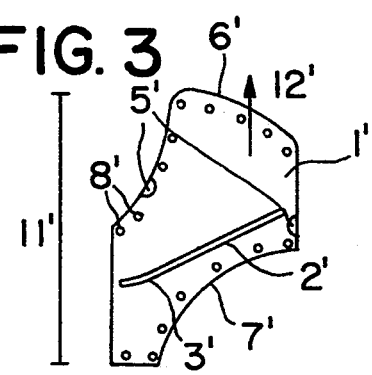
Figure 3A:
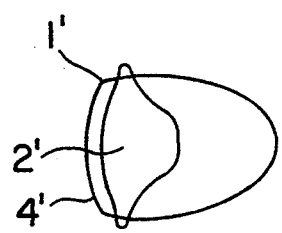
Figure 3B:
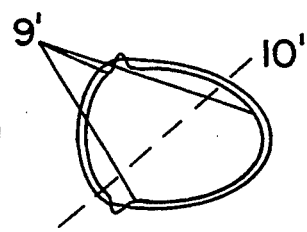
Figure 4:
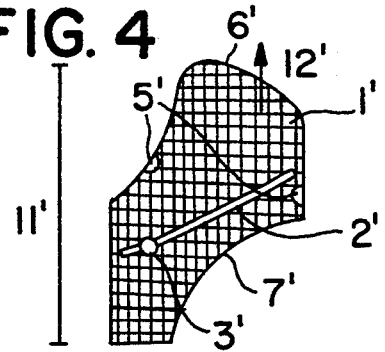
Figure 4A:
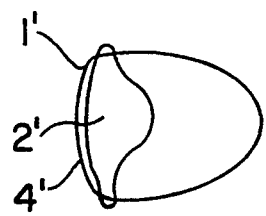
Figure 4B:
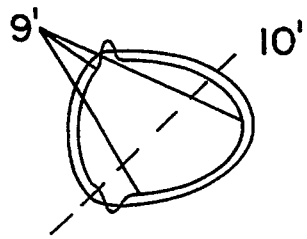

In the drawings FIGS. 1 and 2 show a longitudinal-lateral sectional view of the valve of a semirigid type; FIGS. 3 and 4 are a longitudinal-lateral sectional view of the valve of a rigid type.

With reference to FIGS. 1 and 2.

The valve of a semirigid type has the following main characteristics:
a) the support 1 is cylindrical, of biocompatible plastic material (such as, for example, expanded polytetrafluoroethylene or PTFE, polyester or DACRON etc.) with a mesh or weave which is more or less tight, thin, with ring-shaped or spiral external reinforcements 2. The support can also be formed by a segment of vein (FIG. 2), treated and rendered biocompatible, around which a sleeve of wide meshed plastic material with an external reinforcement as mentioned above is placed.
b) The cylinder is relatively soft and compressible, but the rings and spiral reinforcement 2 render it semirigid and represent a guide for fixing of the valve to the vein. The cylinder can also be modelled during surgery to adapt its shape to the site of implantation.
c) The support 1 contains within its lumen a mobile plate in the form of a monocuspid valve 3 anchored to the support along the line 7.
d) The monocuspid valve, which permits a unidirectional flow 11, is made of the same plastic material as the support, or is made of different material, which can be biologically treated and rendered biocompatible with the receiver (for example pericardium, pleura, mesenteron, collagen or vein, etc.).
e) The monocuspid is extremely thin and practically floats in the lumen, so that it is capable of being moved by relatively low pressures, of the order of 1–50 mmHg (on average 15 mmHg), which result from the difference of pressure on the two sides 4–5 of the mobile plate 3.
f) The free edge 6 (or the floating surface 5) of said plate, both when made of plastic material and when biological, can be reinforced with a filament or other device (of polyethylene, polyester, metal or other substance), provided if necessary with a certain mechanical memory which does not impede the opened position of said plate, shown in FIGS. 1/A, 2/A, and favours the closed position shown in FIGS. 1/B, 2/B, which is mainly obtained from the positive pressure acting on the upper edge 4 of the valve during the muscular diastole of the limb.
g) The valve of a semirigid type is heat-moulded in a ready-made mould, but if the mobile plate 3 is of a different plastic material than the support 1, the plate is heat-welded to the support itself.
h) If the mobile plate 3 is of biological material, it is stitched in the laboratory to the support cylinder along the line 7,
i) The upper insertion point of the monocuspid 8 on the support cylinder is slightly removed from the crossing point of diameter 9 and the circumference so that the free edge is longer than the hemi-circumference of the transverse cross-section (FIGS. 1/B, 2/B) so as to remedy with this increased length the incomplete deflection (during the opening phase) due to the relative rigidity of the insertion point.
l) The internal surface of the valve can be treated with known materials and antithrombogenic processes (pyrolytic or electronegative carbon, heparinized gel, etc.).
m) The dimensions are the following:
diameter 9: approximately 4-6-8-10-12-14 mm
length 10: approximately 14-16-18-20-22-24 mm.

The rigid type valve, FIGS. 3 and 4, has the following main characteristics:
n) The support 1 is metallic of biocompatible alloy or plastic material and has a transverse section shown in FIGS. 1/A, 1/B, 3/A, 4/A in the shape of an irregular ovoid, and a lateral longitudinal section as shown in FIGS. 3 and 4.

o) In its lumen there is a mobile metal plate 2 which allows a unidirectional flow 12, with a hinge 3 close to the base of the ovoid 4. The plate stops, both when opening (FIG. 3/A) and when closing (FIG. 3/B), against special protrusions 5 situated on the inside of the support. Between the support and the mobile plate there is, in all positions, a space 9' of approximately 0.5 mm.

p) The edges of the support are provided with bores 8' of approximately 1 mm in diameter, varying in number according to the caliber of the valve, for passage of the sutures for anchorage to the vein.

q) The shape of the upper edge of the support 6 is such as to allow positioning of the valve immediately upstream of a confluent branch vein.

r) The shape of the lower edge 7' of the support is such as to allow a "window" for the Eco Doppler instrument for bloodless post-operative study of the dynamics and surfaces of the valve.

s) The valve of FIG. 4 differs from that in FIG. 3 as to its rigid support 1', which has an extremely discontinuous or netted surface. This support permits better endotheliation of the valve.

A similar support 1', extremely reticulated, can also be included in a cylindroid of plastic material (for example the PTFE previously mentioned or others); equally the mobile plate 2 can be made of the same plastic material including a rigid reinforcement element: a support and a mobile plate thus constructed can also be continuously joined along base 4 of the cylindroid, as the mobility of the plate is ensured by the flexibility of the plastic joining material.

t) The internal surface of the valve can be treated with the antithrombogenic materials and processes which are already known (pyrolytic or electronegative carbon, heparinized gel, etc.). With the same object, the metal support can be implanted in a vein or other part of living animals and successively explanted and prepared in the laboratory for clinical use in man.

u) The dimensions are the following:

average diameter 10': approximately 8-10-12-14-16 mm.

average length 11': approximately 18-20-22-24-26 mm.

The artificial venous valve according to the present invention, both of the semirigid and of the rigid type and in its various sorts and formations, can be supplied in a sterile packaging ready for use, like the vascular and cardiac prostheses currently in use.

Experimentation and clinical application may suggest variations in shape and size, variation in the materials used or in the antithrombogenic or other treatments, without for this reason departing from the scope of the present invention and therefore from the protection of the relative patent rights.

I claim:

1. An artificial venous valve configured to allow unidirectional flow and to be inserted into a human venous system, biocompatible with the system, comprising:

a hollow elongated support having a predetermined length with a periphery and a predetermined width, said length being greater than said width, said support having openings therethrough for suturing the valve to a vein said support having arcuate edges intersecting linear vertical edges in a longitudinal-lateral sectional view; and a plate carried by and within the support and movable relative to the support between a first position to permit flow of blood in one direction and a second position in which to prevent flow of blood in an opposite direction through said support, said plate in both of said first and second positions being disposed entirely within said support, said plate being movable to open and close over a pressure differential range on opposite sides of said plate of 1–50 mm Hg.

2. An artificial venous valve as recited in claim 1, wherein said plate opens and closes at a pressure differential of about 15 mm Hg.

3. An artificial venous valve as recited in claim 1, having a width of 4–14 mm and a length of 14–24 mm.

* * * * *